United States Patent [19]
Mizukami et al.

[11] Patent Number: 5,798,379
[45] Date of Patent: Aug. 25, 1998

[54] UCS1025 COMPOUNDS

[75] Inventors: Tamio Mizukami; Harumi Ogawa; Ryuichiro Nakai, all of Tokyo; Akira Asai, Kanagawa; Yoshinori Yamashita; Katsuhiko Ando, both of Tokyo; Tsutomu Agatsuma; Shiro Akinaga, both of Shizuoka; Kozo Ouchi, Saitama; Hideki Kawasaki, Ibaraki, all of Japan

[73] Assignee: Kyowa Hakko Kogyo Co., Ltd., Tokyo, Japan

[21] Appl. No.: 994,029

[22] Filed: Dec. 18, 1997

[30] Foreign Application Priority Data

Dec. 18, 1996 [JP] Japan ................................. 8-337765
Jan. 6, 1997 [JP] Japan ................................. 9-000120

[51] Int. Cl.⁶ ........................... A61K 31/40; C07D 487/02
[52] U.S. Cl. ........................... 514/441; 548/428; 435/119
[58] Field of Search ........................... 548/428; 514/441; 435/119

[56] References Cited

PUBLICATIONS

West et al., The Journal of Antibiotics, vol. 49, No. 10 (1966) 967–973.

*Primary Examiner*—Fiona T. Powers
*Attorney, Agent, or Firm*—Fitzpatrick, Cella, Harper & Scinto

[57] ABSTRACT

UCS1025 compounds represented by the following formula (I):

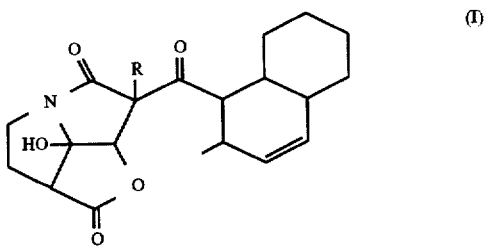

wherein R represents hydrogen or hydroxyl group, or tautomers or pharmacologically acceptable salts thereof.

5 Claims, No Drawings

UCS1025 COMPOUNDS

BACKGROUND

1. Filed of the Invention The present invention relates to UCS1025 compounds, tautomers chemically equivalent thereto, and pharmacologically acceptable salts thereof. These materials have antibacterial and antitumor activities and are useful as antibacterial agents and antitumor agents.

2. Brief Description of the Background Art

Several compounds such as ZG-1494α represented by the following formula (IV) have been reported [*Journal of Antibiotics*, 49, 967 –973 (1996)]:

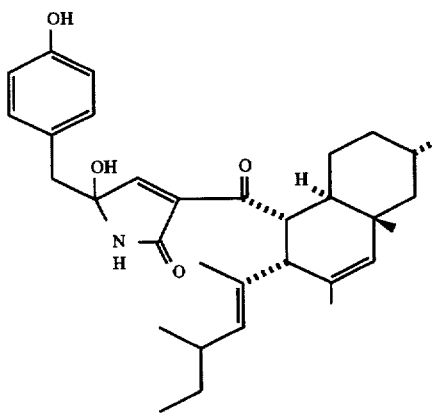

SUMMARY OF THE INVENTION

An object of the present invention is to provide compounds which have excellent antibacterial and antitumor activities.

This and other objects of the present invention have been accomplished by UCS1025 compounds represented by the following formula (I):

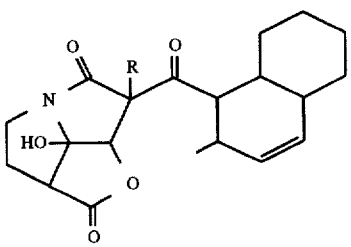

(wherein R represents hydrogen or hydroxyl group), tautomers chemically equivalent thereto, or pharmacologically acceptable salts thereof, which compounds, tautomers and salts have antibacterial and antitumor activities. The present invention also relates to a pharmaceutical composition comprising a pharmaceutically acceptable carrier and as an active ingredient, an effective amount of one of the compounds, tautomers or salts (referred to hereinafter collectively as "UCS1025 compounds") defined above.

DETAILED DESCRIPTION OF THE INVENTION

This application is based on Japanese application Nos. Hei 8-337765 filed on Dec. 18, 1996 and Hei 9-102 filed on Jan. 6, 1997, the entire contents of which are incorporated hereinto by reference.

In formula (I), a compound in which R is hydrogen is called UCS1025A, and a compound in which R is hydroxyl group is called UCS1025B.

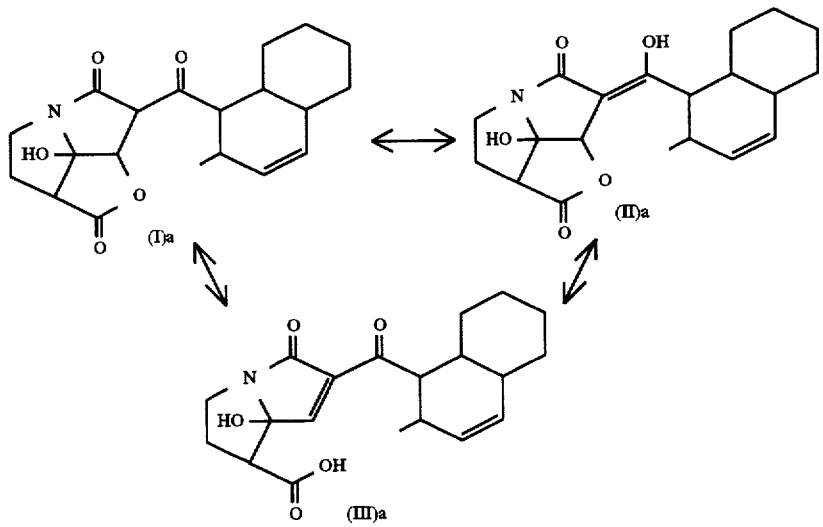

UCS1025A exists as an equilibrium mixture of three compounds such as a keto type (I)a, an enol type (II)a, and a carboxyl type (III)a, and their composition ratio widely varies depending on the conditions, such as solvent, temperature and the like. Such tautomers, stereoisomers thereof and mixtures of these compounds at all ratios are included in the present invention.

The physicochemical properties of UCS1025 compounds are shown below. As mentioned above, the present compounds exist as a mixture of tautomers chemically equivalent thereto. Accordingly, the mixture ratios of these compounds widely vary depending on the conditions of sample obtaining and measuring and are not definite. The following data relate to the samples which were obtained by the methods shown in the following examples. In $^1$H- and $^{13}$C-nuclear magnetic resonance spectrum, each signal of the tautomers are possible to measure and distinguish, so the data of these tautomers are shown separately. The physico-chemical properties were measured by the following apparatus:

Melting point:
  Yanagimoto Seisakusyo: Micro measuring apparatus of melting point
Optical rotation:
  Nippon Bunko Kogyo: DIP-370 Digital polarimeter
FAB mass spectrum and high resolution FAB mass spectrum:
  JEOL: JMS-HX/HX110A Mass spectrum
Ultraviolet absorption spectrum:
  Shimadzu Corporation: UV-2200 Spectrophotometer
Infrared absorption spectrum:
  JEOL: JIR-RFX-3001 Infrared spectrophotometer
Nuclear magnetic resonance spectrum:
  JEOL: JNM-A400 Nuclear magnetic resonance apparatus Physicochemical data of UCS1025A:
Color and form of the substance:
  Colorless acicular crystal
Melting point:
  135 to 137° C.
Optical rotation:

$[\alpha]_D^{28} = 30.1°(c=0.1, CH_3OH)$

Molecular formula:

$C_{20}H_{25}NO_5$

FAB mass spectrum:

m/z 360 [M+H]$^+$

High resolution FAB mass spectrum:
  Calculated: 360.1799
  Theoretical: 360.1811 (for $C_{20}H_{26}NO_5$)
Ultraviolet absorption spectrum (CH$_3$OH):

$\lambda$max ($\epsilon$) 260 (7,100) nm

Infrared absorption spectrum (KBr):
  vvmax 3440, 2920, 2850, 1790, 1670, 1445, 1415, 1385, 1320, 1235, 1160, 1110, 1020, 970 cm$^{-1}$
$^1$H NMR spectrum:
  keto-type σ (CDCl$_3$): 5.59 (1H, ddd, J=2.6, 4.7, 9.8 Hz), 5.41 (1H, br d, J=9.8 Hz), 4.754 (1H, s), 4.746 (1H, s), 4.05 (1H, s), 3.84 (1H, ddd, J=5.9, 9.3, 12.0 Hz), 3.36 (1H, ddd, J=5.3, 9.8, 12.0 Hz), 3.25 (1H, dd, J=2.1, 9.3 Hz), 3.18 (1H, dd, J=5.4, 11.2 Hz), 2.91 (1H, m), 2.74 (1H, m), 2.56 (1H, m), 1.77 (5H, m), 1.51 (1H, m), 1.33 (2H, m), 1.09 (1H, m), 0.89 (1H, m), 0.79 (3H, d, J=7.1 Hz) ppm
  enol-type δ (CDC$_3$): 11.88 (1H, br s), 5.55 (1H, ddd, J=2.7, 4.2, 10.0 Hz), 5.39 (1H, br d, J=10.0 Hz), 5.29 (1H,s), 3.93 (1H, m), 3.45 (1H, m), 3.30 (1H, dd, J=4.4, 10.0 Hz), 2.70 (1H, m), 2.68 (1H, m), 2.56 (1H, m), 2.50 (1H, m), 1.88 (1H, br d, J=12.9 Hz), 1.77 (4H, m), 1.58 (1H, m), 1.33 (2H, m), 1.13 (1H, m), 1.00 (3H, d, J=6.8 Hz), 0.91 (1H, m) ppm
  carboxyl-type σ (100 mM phosphoric acid buffer [pH 6] : D$_2$O=4 : 1, v/v): 7.83 (1H, s), 5.44 (1H, d, J=9.8 Hz), 3.58 (1H, dt, J=10.9, 8.7 Hz), 3.40 (1H, dd, J=5.9, 11.2 Hz), 3.24 (1H, ddd, J=3.0, 9.4, 10.9 Hz), 2.99 (1H, dd, J=1.5, 7.0 Hz), 2.46–2.55 (1H, m), 2.46–2.55 (1H, m), 2.36–2.41 (1H, m), 1.61–1.81 (5H, m), 1.45 (1H, m), 1.22–1.35 (2H, m), 0.98 (1H, m), 0.80 (1H, m), 0.63 (3H, d, J=7.1 Hz) ppm $^{13}$C NMR spectrum: δ (CDCl$_3$)
  keto-type: 208.5 (s), 174.5 (s), 167.1 (s), 130.7 (d), 130.4 (d), 101.0 (s), 80.3 (d), 66.4 (d), 58.8 (d), 47.7 (d), 42.2 (d), 41.8 (t), 36.8 (d), 32.9 (t), 30.2 (d), 30.0 (t), 29.9 (t), 26.52 (t), 26.46 (t), 17.6 (q) ppm
  enol-type: 192.7 (s), 131.6 (d), 130.3 (d), 102.1 (s), 100.7 (s), 81.3 (d), 48.8 (d), 47.6 (d), 44.4 (t), 42.7 (d), 36.0 (d), 34.8 (d), 33.1 (t), 31.5 (t), 30.4 (t), 26.7 (t), 26.5 (t), 17.9 (q) ppm Solubility:
  Soluble in methanol, ethyl acetate, chloroform, dimethylsulfoxide (DMSO); hardly soluble in hexane
Color reagent:
  Positive for iodine reagent, sulfuric acid ethanol reagent and phosphomolybdic acid/sulfuric acid cerium reagent
Thin-layer chromatography:
Rf value:
  0.39
Thin-layer:
  silica gel TLC (produced by Merck Co.)
Developing solvent:

hexane : acetone =2 : 1 (v/v)

Thin-layer chromatography:
Rf value:
  0.80
Thin-layer:
  silica gel TLC (produced by Merck Co.)
Developing solvent:

ethyl acetate : acetic acid =99 : 1 (v/v)

Physicochemical data of UCS1025B:
Color and form of the substance:
  Colorless acicular crystal
Melting point:
  221 to 223° C.
Optical rotation:

$[\alpha]_D^{28} = -31.8°$ (c=0.1, CH$_3$OH)

Molecular formula:

$C_{20}H_{25}NO_6$

FAB mass spectrum:

m/z 376 [M+H]d$^+$

High resolution FAB mass spectrum:
  Calculated: 376.1757
  Theoretical: 376.1760 (for $C_{20}H_{25}NO_6$)
Ultraviolet absorption spectrum:
  Only end absorption is shown
Infrared absorption spectrum (KBr):

vvmax 3205, 2925, 2875, 1805, 1720, 1670, 1410, 1325, 1300, 1175, 1130, 1040 cm$^{-1}$ ¹H NMR spectrum:

δ(CDCl₃) 5.54 (1H, ddd, J=2.4, 4.6, 9.8 Hz), 5.36 (1H, br d, J=9.8 Hz), 5.13 (1H, s), 4.36 (1H, s), 3.83 (1H, ddd, J=6.7, 9.3, 12.0 Hz), 3.46 (1H, ddd, J=4.4, 9.8, 12.0 Hz), 3.43 (1H, s), 3.21 (2H, m), 2.94 (1H, m), 2.78 (1H, m), 2.64 (1H, dddd, J=1.7, 4.4, 9.0, 13.7 Hz), 1.80 (1H, m), 2.64 (1H, m), 1.72 (2H, m), 1.63 (1H, m), 1.38 (1H, m), 1.30 (2H, m), 1.13 (1H, m), 1.05 (1H, m), 0.89 (3H, d, J=7.1 Hz) ppm ¹³C NMR spectrum:

δ (CDCl₃) 207.7 (s), 173.7 (s), 168.6 (s), 131.1 (d), 130.4 (d), 100.7 (s), 85.0 (s), 83.5 (d), 53.7 (d), 46.9 (d), 42.2 (d), 41.2 (t), 38.7 (d), 33.2 (t), 31.2 (d), 29.31 (t), 29.28 (t), 26.7 (t), 26.4 (t), 17.5 (q) ppm Solubility:

Soluble in methanol, ethyl acetate, chloroform, DMSO; hardly soluble in hexane

Color reagent:

Positive for iodine reagent, sulfuric acid ethanol reagent and phosphomolybdic acid/sulfuric acid cerium reagent Thin-layer chromatography:

Rf value:

0.28

Thin-layer:

silica gel TLC (produced by Merck Co.)

Developing solvent:

hexane : acetone =2 : 1 (v/v)

Biological activities of UCS1025 compounds are described by the following test examples.

UCS1025 compounds can be obtained by culturing in a medium a microorganism belonging to the genus Acremonium or Humicola and having the ability to produce UCS1025 compounds, thereby allowing UCS1025 compounds to accumulate in the culture, and recovering them from the culture.

As the microorganism having the ability to produce UCS1025 compounds, any strain can be used, insofar as it belongs to the genus Acremonium or Humicola and can produce UCS1025 compounds. Also, any mutant of such strains which are obtained by various artificial mutation methods, such as ultraviolet ray irradiation, X-ray irradiation, mutagen treatment or the like, or by spontaneous mutation can be used in the present invention, insofar as they have the ability to produce UCS1025 compounds. Examples of preferred strains include Acramonium sp. KPC 7629-19 strain and Humicola sp. KPC 7781-6 strain.

The inventors of the present invention have found that a fungal strain KPC 7629-19 belonging to the genus Acremonium and a fungal strain KPC 7781-6 belonging to the genus Humicola, newly isolated from soil, can produce UCS1025 compounds having antibacterial and antitumor activities.

A typical strain (KPC 7629-19) capable of producing the compound of the present invention has been isolated from a soil sample, and the mycological properties thereof are as follows:

1. Macroscopic observation

When the strain is cultured at 25° C. on malt extract agar media, the diameter of a colony reaches 16 to 21 mm on the 7th day of culturing and 28 to 31 mm on the 14th day of culturing. Central part of the colony surface shows a grayish brown color and its peripheral is beige or grayish white. Central part of the reverse side of the colony shows a reddish brown color and its peripheral is beige or grayish liver brown. Also, it produces an orange pigment in the media.

When the strain is cultured at 25° C. on potato-glucose agar media, the diameter of a colony reaches about 15 mm on the 7th day of culturing and about 25 mm on the 14th day of culturing. Central part of the colony surface becomes a radial wrinkled shape and shows a cream to brown color and its peripheral is gray. Central part of the reverse side of the colony shows a light brown to liver brown color and its peripheral is grayish white. - The growth temperature range for this strain is 11 to 31° C., and the optimum growth temperature is around 23° C. The pH range which allows its growth is 3 to 10, and the optimum growth pH is around 6.

2. Optical microscopic observation

Results of the observation of this strain under a optical microscope after culturing at 25° C. for 2 weeks on potato-glucose agar media are as follows.

Its hyphae have septa, are smooth and branch well. Its conidia are formed from phialide generated from the side or top of the hypha. Single phialide is generated from each hypha, which is colorless, smooth and conical, and the base part is 1.5 to 2.5 μm width and gradually becomes thin toward its tip which has a width of 0.5 to 1.5 μm. The phialide is 10 to 35 μm long and has a septum in its base part. Entero blastic-phialidic conidia are formed from the tip of phialide, and conidia adhering in slimy droplets conidiophore is generally formed on the tip of the phialide. The conidium is subspherical to elliptical, colorless and smooth and is 2.5 to 4.5 μm long and 1.7 to 2.5 μm wide. Also, it forms a spherical to subspherical chlamydospore having 2.5 to 5.5 μm diameter.

No teleomorph but only the aforementioned anamorph can be observed in this strain.

On the basis of these mycological properties, taxonomic position of this strain was checked in accordance with "The Genera of Fungi Sporulating in Pure Culture, 2nd ed., Cramer, Vaduz, J.A. von Arx, 1974", and found as the results that this strain belongs to the genus Acremonium of .Hyphomycetes. The present inventors have named this strain as "Acremonium sp. KPC 7629-19" and deposited in National Institute of Bioscience and Human Technology (Higashi 1-1-3,Tsukuba, Ibaraki), Agency of Industrial Science and Technology, the Ministry of International Trade and Industry on Sep. 26, 1996 with accession number FERM BP-5673. In this connection, the species belonging to the genus Acremonium are described in detail in "Cephalosporium-artige Schimmelpilze (Hyphomycetes), (Gustav Fischer Verlag, Stuttgart, 1971) written by Walter Gams".

Another typical strain (KPC 7781-6) capable of producing the compounds of the present invention has been also isolated from a soil sample, and it has the following mycological properties.

1. Macroscopic observation

When the strain is cultured at 25° C. on malt extract agar media, diameter of colony reaches 40 to 50 mm on the 7th day of culturing and 63 to 75 mm on the 14th day of culturing. The surface of the colony is slightly greenish and grayish white to gray and its peripheral is blackish brown. The reverse side of the colony shows a blackish brown color and its peripheral sometimes shows a creamy color.

When the strain is cultured at 25° C. on potato-glucose agar media, the diameter of the colony reaches 39 to 46 mm on the 7th day of culturing and 65 to 70 mm on the 14th day of culturing. Central part of the colony surface is white and the peripheral is blackish gray. The reverse side of the colony shows a blackish brown color and the central part sometimes shows a beige color.

The growth temperature range for this strain is 11 to 33° C., and the optimum growth temperature is at around 27° C. It can grow at pH 3 to 12, and the optimum growth pH is around 6.

2. Optical microscopic observation

Results of the observation of this strain under an optical microscope after culturing at 25° C for 2 weeks on malt extract agar media are as follows.

Its hyphae have septa, are smooth and branch frequently. Its conidia are formed from hyphae or short conidiophores. Single conidium is formed into aleuro type from the tip of the conidium-forming cell by exogenous budding. The mature conidium is a spherical to subspherical single cell, shows a light brown to dark brown color, is smooth and 6.5 to 9.5 μm diameter. Occasionally, a club-like or broad club-like conidium and a double cell-type conidium are formed.

No teleomorph but only the aforementioned anamorph can be observed in this strain.

On the basis of these mycological properties, taxonomic position of this strain was checked in accordance with "*The Genera of Fungi Sporulating in Pure Culture*, 2nd ed., Cramer, Vaduz, J.A. von Arx, 1974", and found as the results that this strain belongs to the genus Humicola of Hyphomycetes. The present inventors have named this strain as "Humicola sp. KPC 7781-6" and deposited in National Institute of Bioscience and Human Technology (Higashi 1-1-3, Tsukuba, Ibaraki), Agency of Industrial Science and Technology, the Ministry of International Trade and Industry on Sep. 26, 1996 with accession number FERM BP-5674.

In the culturing the UCS1025 compound-producing strains of the present invention, usually used fungi culturing method can be employed. As the medium, either a synthetic medium or a natural medium can be used, insofar as it properly, for example, contains carbon sources, nitrogen sources, inorganic compounds and the like which can be assimilated by the strains employed.

Examples of the carbon sources include glucose, starch, dextrin, mannose, fructose, sucrose, lactose, xylose, arabinose, mannitol, molasses and the like, which may be used alone or in combination thereof. Depending on the assimilation ability of the strains, hydrocarbons, alcohols, organic acids and the like can also be used.

Examples of the nitrogen sources include ammonium chloride, ammonium nitrate, ammonium sulfate, sodium nitrate, urea, peptone, meat extract, yeast extract, dry yeast, corn steep liquor, soybean powder, casamino acid and the like, which may be used alone or as a mixture thereof.

In addition to the above, sodium chloride, potassium chloride, magnesium sulfate, calcium carbonate, potassium dihydrogenphosphate, magnesium phosphate octahydrate, ferrous sulfate, calcium chloride, manganese sulfate, zinc sulfate, copper sulfate and the like inorganic salts may be added as occasion demands. Also, minor components which enhance growth of the strain or production of UCS1025 compounds may be added appropriately.

With regard to the culturing methods, a liquid culture method, particularly a submerged stirring culture method, is suitable. Culturing is carried out at 16 to 37° C., preferably 25 to 32° C., and at pH 4 to 10, preferably 6 to 8, and liquid ammonia, ammonium carbonate aqueous solution and the like are used for adjusting the medium pH. The culturing is completed generally after 1 to 9 days, but it is desirable to terminate the culturing when UCS1025 compound are formed and accumulated in the culture broth and cells and the produced amount in the culture mixture reaches the maximum.

Isolation and purification of the thus accumulated UCS1025 compounds from the culture can be effected by employing appropriate methods which are generally used for isolating and purifying usual microbial metabolites from the culture.

For example, the culture is separated into culture filtrate and cells by filtration, and cell components are extracted from the cells with chloroform, acetone or the like solvent. Next, the extract and culture filtrate are combined and applied to a polystyrene based adsorbent such as Diaion HP-20 (manufactured by Mitsubishi Chemical Corp.) to effect adsorption of the active component which is subsequently eluted with methanol, acetone or the like solvent. Thereafter, UCS1025 compounds are obtained by concentrating the eluate and treating it, for example, with octadecyl group-bonded type silica gel (ODS) column chromatography, high-performance liquid chromatography or silica gel column chromatography. In this connection, detection of UCS1025 compounds during the culturing and isolation purification steps can be made by a thin layer chromatography and subsequent iodine reagent treatment.

Pharmacologically acceptable salts of UCS1025 compounds or tautomers of chemically equivalent thereto include pharmacologically acceptable metal salts, ammonium salts, organic amine addition salts and amino acid addition salts. Examples of the metal salts include alkali metal salts (e.g., lithium salts, sodium salts, potassium salts), alkaline earth metal salts (e.g., magnesium salts, calcium salts), aluminum salts, zinc salts and the like. Examples of the ammonium salts include salts of ammonium, tetramethylammonium and the like. Examples of the organic amine addition salts include addition salts of morpholine, piperidine and the like. Examples of the amino acid addition salts include addition salts of glycine, phenylalanine, aspartic acid, glutamic acid, lysine and the like.

When it is desirable to obtain salts of UCS1025 compounds or tautomers chemically equivalent thereto, they may be purified as such if salts of the UCS1025 compound or its chemically equivalent tautomers can be obtained, or when they are obtained in their free forms, they may be dissolved or suspended in an appropriate solvent and then made into salts by adding a base.

In addition, UCS1025 compounds, tautomers chemically equivalent thereto or pharmacologically acceptable salts thereof may exist in some cases in the form of addition products with water or various solvents, and these addition products are also included in the present invention.

According to the present invention, UCS1025 compounds having antibacterial and antitumor activities, tautomers chemically equivalent thereto or pharmacologically acceptable salts thereof can be provided.

EXAMPLES

Examples of the present invention are given below by way of illustration and not by way of limitation.

Production Example 1

Production of UCS1025A and UCS1025B by Acremonium sp. KPC 7629-19 strain:

A medium (pH 6.5) composed of 100 g/L glucose, 30 g/L mashed potato base and 5 g/L yeast extract was used as the first and second seed culture media. One loopful of seed strain was inoculated into 50 ml of the first seed medium contained in a 300 ml capacity conical flask and cultured at 25° C. for 144 hours on a shaker. A 15 ml portion of the thus obtained first seed culture (50 ml) broth was inoculated into 300 ml of the second seed medium contained in each of six 2 L capacity conical flasks and cultured with shaking at 25° C. for 48 hours. A 900 ml portion of the thus obtained second seed culture broth was inoculated into 18 L of a main fermentation medium contained in each of two 30 L capacity tank (36 L in total) and cultured at 25° C. for 162 hours with aeration and agitation (agitation speed 300 rpm, aeration rate 18 L/min). A medium (pH 6.0) composed of 20 g/L glucose, 20 g/L mashed potato base, 5 g/L peptone, 5 g/L potassium dihydrogenphosphate and 0.5 g/L magnesium phosphate octahydrate was used as the main fermentation medium.

A 30 L portion of the thus obtained fermentation broth was mixed with 10% of a filter aid (Radiolite #600, manufactured by Showa Chemical Industry) and filtered using a centrifugal filter. The culture filtrate thus separated from the cells was applied to a column packed with 2 L of Diaion HP-20 to effect adsorption of the active components. Impurities were eluted with 6 L of 40% methanol aqueous solution and then the active components were eluted with 6 L of methanol. The active fraction was concentrated to 400 ml under a reduced pressure. This was mixed with the same volume of ethyl acetate to extract the active components. When the extract was concentrated to dryness under a reduced pressure, a brown oily substance was obtained. Using a silica gel column (Wako Gel C-200, manufactured by Wako Pure Chemical Industries), this oily substance was developed with a hexane-ethyl acetate mixture solution. Impurities were eluted with a hexane/ethyl acetate (7:3, v/v) solution and then the active components were eluted with a hexane/ethyl acetate (6:4-5:5, v/v) solution. When the active fraction was concentrated to dryness, a light brown oily substance was obtained. Using a silica gel column (LiChroprep Si 60, manufactured by Merck), this was developed with a hexane-acetone mixture solution. Impurities were eluted with a hexane/acetone (86:14, v/v) solution and then UCS1025A fraction was eluted with a hexane/acetone (84:16-82:18, v/v) solution. Thereafter, UCS1025B fraction was eluted with a hexane/acetone (80:20 - 75:25, v/v) solution. Both of the fractions of UCS1025A and UCS1025B were allowed to stand for 3 days at 4° C. for crystallization. By recovering and drying the thus precipitated crystals, 131 mg of UCS1025A and 4.8 mg of UCS1025B were obtained.

Production Example 2

Production of UCS1025A by Humicola sp. KPC 7781-6 strain:

UCS1025A was produced using Humicola sp. KPC 7781-6 strain as the seed strain.

A medium (pH 6.5) composed of 100 g/L glucose, 30 g/L mashed potato base and 5 g/L yeast extract was used as the seed culture medium. One loopful of the seed strain was inoculated into 50 ml of seed culture medium contained in a 300 ml capacity conical flask and cultured with shaking at 25° C. for 72 hours. A 2.5 ml portion of the thus obtained culture broth was inoculated into 50 ml of a main fermentation medium contained in each of 300 ml capacity conical flasks (40 flasks, 2 L in total) and cultured with shaking at 25° C. for 216 hours. A medium (pH 6.0) composed of 20 g/L glucose, 20 g/L mashed potato base, 5 g/L peptone, 5 g/L potassium dihydrogenphosphate and 0.5 g/L magnesium phosphate octahydrate was used as the main fermentation medium.

A 2 L portion of the thus obtained fermentation broth was mixed with 10% of a filter aid (Radiolite #600, manufactured by Showa Chemical Industry) and filtered using a suction filter. The cells thus separated from the culture filtrate were mixed with 1 L of methanol and thoroughly stirred to effect extraction and again filtered using the suction filter. The thus obtained methanol extract was concentrated under a reduced pressure and then adjusted to 1 L by adding water. This solution and the culture filtrate were separately applied to a column packed with Diaion HP-20, and the active component was eluted with methanol. Both of the active fractions were combined, concentrated under a reduced pressure and then adjusted to 5 L by adding water. This was applied to a column packed with Diaion HP-20ss and developed with a water-methanol mixture solution. Impurities were eluted with a water/methanol (3:7, v/v) solution and then the active component was eluted with a water/methanol (2:8 - 0:1, v/v) solution. When the active fraction was concentrated to dryness under a reduced pressure, a brown oily substance was obtained. Using a silica gel column (Wako Gel C-200, manufactured by Wako Pure Chemical Industries), this oily substance was developed with a chloroform-methanol-acetic acid mixture solution. Impurities were eluted with a chloroform/methanol/acetic acid (1000:10:1, v/v/v) solution and then the active component was eluted with a chloroform/methanol/acetic acid (980:20:2, v/v/v) solution. When the active fraction was concentrated to dryness, a light brown oily substance was obtained. Using the silica gel column (Wako Gel C-200, manufactured by Wako Pure Chemical Industries), this was again developed with a hexane-acetone mixture solution. Impurities were eluted with a hexane/acetone (9:1, v/v) solution and then the active component was eluted with a hexane/acetone (8:2, v/v) solution. Thereafter, the active fraction was concentrated to dryness and subjected to FAB mass spectrum analysis, HPLC analysis and TLC analysis. As the results, it was found that this active component was identical to UCS1025A. It was confirmed that UCS1025A can also be produced using Humicola sp. KPC 7781-6 as the seed strain.

Test Example 1

Antibacterial activity upon various bacteria:

Antibacterial activity of UCS1025A and UCS1025B against various bacteria were measured.

The antibacterial activity was measured by an agar dilution method on media (pH 7) -composed of 3 g/L of Bacto-tryptone (manufactured by Difco), 3 g/L of meat extract, 1 g/L of yeast extract, 1 g/L of glucose and 16 g/L of agar. The antibacterial activity was shown by minimum inhibitory concentration (MIC).

The results are shown in Table 1.

TABLE 1

| Strains tested | Minimum inhibitory concentration (µg/ml) | |
| --- | --- | --- |
| | UCS1025A | UCS1025B |
| Staphylococcus aureus ATCC 6538P | 1.3 | 42 |
| Bacillus subtilis No. 10707 | 1.3 | 83 |
| Enterococcus hirae ATCC 10541 | 1.3 | 42 |
| Proteus vulgaris ATCC 6897 | 5.2 | 83 |

Test Example 2

Growth inhibition against human mammary carcinoma MCF-7, human cystocarcinoma T24, human epidermoid carcinoma A431 and human renal carcinoma ACHN cells:

Respective cells were dispensed into a 96 well microtiter plate (Nunc #167008) in $1 \times 10^3$ cells/well portions in the case of MCF-7 and T24 or in $1.5 \times 10^3$ cells/well portions in the case of A431 and ACHN and cultured at 37° C. for 24 hours in a 5% carbon dioxide incubator. Thereafter, 30 mM of UCS1025A and 30 mM of UCS1025B were each serially diluted and added to the wells in 50 µl portions. The final concentration of each solution becomes 100 µM at the maximum at this stage. They were cultured again at 37° C. for 72 hours in the 5% carbon dioxide incubator. Five hours prior to the completion of the culturing, MTT [3-(4,5-dimethylthiazo-2-yl)-2,5-diphenyltetrazolium bromide, Sigma] which had been dissolved in the culture to a final concentration of 1 mg/ml was dispensed into the plate in 50 μl/well portions. After completion of the culturing, DMSO was dispensed in 150 μl/well portions, and the resulting plate was stirred vigorously using a plate mixer to dissolve MTT-formazan crystals completely. Thereafter, absorbance at 550 nm was measured using a microplate spectrophotometer M-SPmax250 (manufactured by Wako Pure Chemical Industries). The cell growth inhibition activity was shown by the 50% inhibitory concentration $IC_{50}$ The results are shown in Table 2.

TABLE 2

| Compound | $IC_{50}$ (μM) | | | |
| --- | --- | --- | --- | --- |
| | MCF-7 | T24 | A431 | ACHN |
| UCS1025A | 21 | 51 | 55 | 58 |
| UCS1025B | >100 | >100 | >100 | >100 |

While the invention has been described in detail and with reference to specific embodiments thereof, it will be apparent to one skilled in the art that various changes and modifications can be made therein without departing from the spirit and scope thereof.

What is claimed is:

1. A UCS1025 compound represented by the following formula (I):

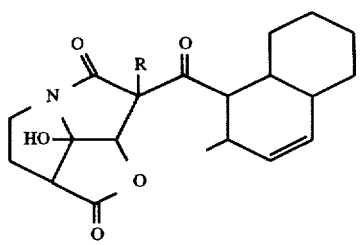

wherein R represents hydrogen or hydroxyl group, or tautomers or pharmacologically acceptable salts thereof.

2. A pharmaceutical composition comprising a pharmaceutically acceptable carrier and an effective amount of a compound as defined by claim 1.

3. The pharmaceutical composition according to claim 2, wherein R is a hydrogen.

4. The pharmaceutical composition according to claim 2, wherein R is a hydroxyl group.

5. A process for producing a UCS1025 compound according to claim 1, comprising culturing a microorganism belonging to the genus Acremonium or Humicola capable of producing said compound, and isolating said compound from the culture.

* * * * *